US012672855B2

(12) United States Patent
Tabata et al.

(10) Patent No.: US 12,672,855 B2
(45) Date of Patent: Jul. 7, 2026

(54) PHYSIOLOGICAL INFORMATION PROCESSING METHOD, PHYSIOLOGICAL INFORMATION PROCESSING APPARATUS AND NON-TRANSITORY COMPUTER READABLE STORAGE MEDIUM

(71) Applicant: NIHON KOHDEN CORPORATION, Tokyo (JP)

(72) Inventors: Hiraku Tabata, Tokorozawa (JP); Mitsuhiro Oura, Tokorozawa (JP); Sou Kumagai, Tokorozawa (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 43 days.

(21) Appl. No.: 18/684,579

(22) PCT Filed: Aug. 15, 2022

(86) PCT No.: PCT/JP2022/030904

§ 371 (c)(1),
(2) Date: Feb. 16, 2024

(87) PCT Pub. No.: WO2023/022133

PCT Pub. Date: Feb. 23, 2023

(65) Prior Publication Data

US 2024/0382179 A1    Nov. 21, 2024

(30) Foreign Application Priority Data

Aug. 20, 2021    (JP) ................................. 2021-134859

(51) Int. Cl.
| | |
|---|---|
| *A61B 8/00* | (2006.01) |
| *A61B 8/06* | (2006.01) |
| *A61B 8/08* | (2006.01) |

(52) U.S. Cl.
CPC ................ *A61B 8/488* (2013.01); *A61B 8/06* (2013.01); *A61B 8/08* (2013.01)

(58) Field of Classification Search
CPC .................................. A61B 8/488; A61B 8/06
See application file for complete search history.

(56) References Cited

U.S. PATENT DOCUMENTS

2006/0241427 A1    10/2006   Kinouchi et al.
2014/0228688 A1    8/2014    Gupta et al.
(Continued)

FOREIGN PATENT DOCUMENTS

| EP | 2 725 983 A2 | 5/2014 |
|---|---|---|
| EP | 3 024 396 A1 | 6/2016 |

(Continued)

OTHER PUBLICATIONS

International Search Report (PCT/ISA/210) issued Nov. 11, 2022 by the International Searching Authority in International Patent Application No. PCT/JP2022/030904.
(Continued)

*Primary Examiner* — Rochelle D Turchen
(74) *Attorney, Agent, or Firm* — Sughrue Mion, PLLC

(57) ABSTRACT

A physiological information processing method for automatically acquiring information relevant to a fluid flowing through a body of a subject using an ultrasonic sensor. The ultrasonic sensor includes a plurality of ultrasonic elements. The physiological information processing method includes acquiring reflection signals of ultrasonic waves, identifying, among the ultrasonic elements, two or more ultrasonic elements facing a vessel through which the fluid flows, analyzing a reflection signal of an ultrasonic wave associated with a first ultrasonic element of the two or more ultrasonic elements, analyzing a reflection signal of an ultrasonic wave associated with a second ultrasonic element
(Continued)

of the two or more ultrasonic elements, identifying an angle of the vessel with respect to the irradiation direction of the ultrasonic wave, analyzing the reflection signal of the ultrasonic wave associated with the first ultrasonic element or the second ultrasonic element, and acquiring information relevant to the fluid.

14 Claims, 7 Drawing Sheets

(56) References Cited

U.S. PATENT DOCUMENTS

2016/0157826  A1      6/2016  Sisodia et al.
2021/0275150  A1 *    9/2021  Ban .......................... A61B 8/54

FOREIGN PATENT DOCUMENTS

| JP | 2017-86726  A | 5/2017 |
|---|---|---|
| WO | 2013/001503  A2 | 1/2013 |
| WO | 2015/011594  A1 | 1/2015 |

OTHER PUBLICATIONS

Written Opinion (PCT/ISA/237) issued Nov. 11, 2022 by the International Searching Authority in International Patent Application No. PCT/JP2022/030904.

* cited by examiner

*FIG. 4*

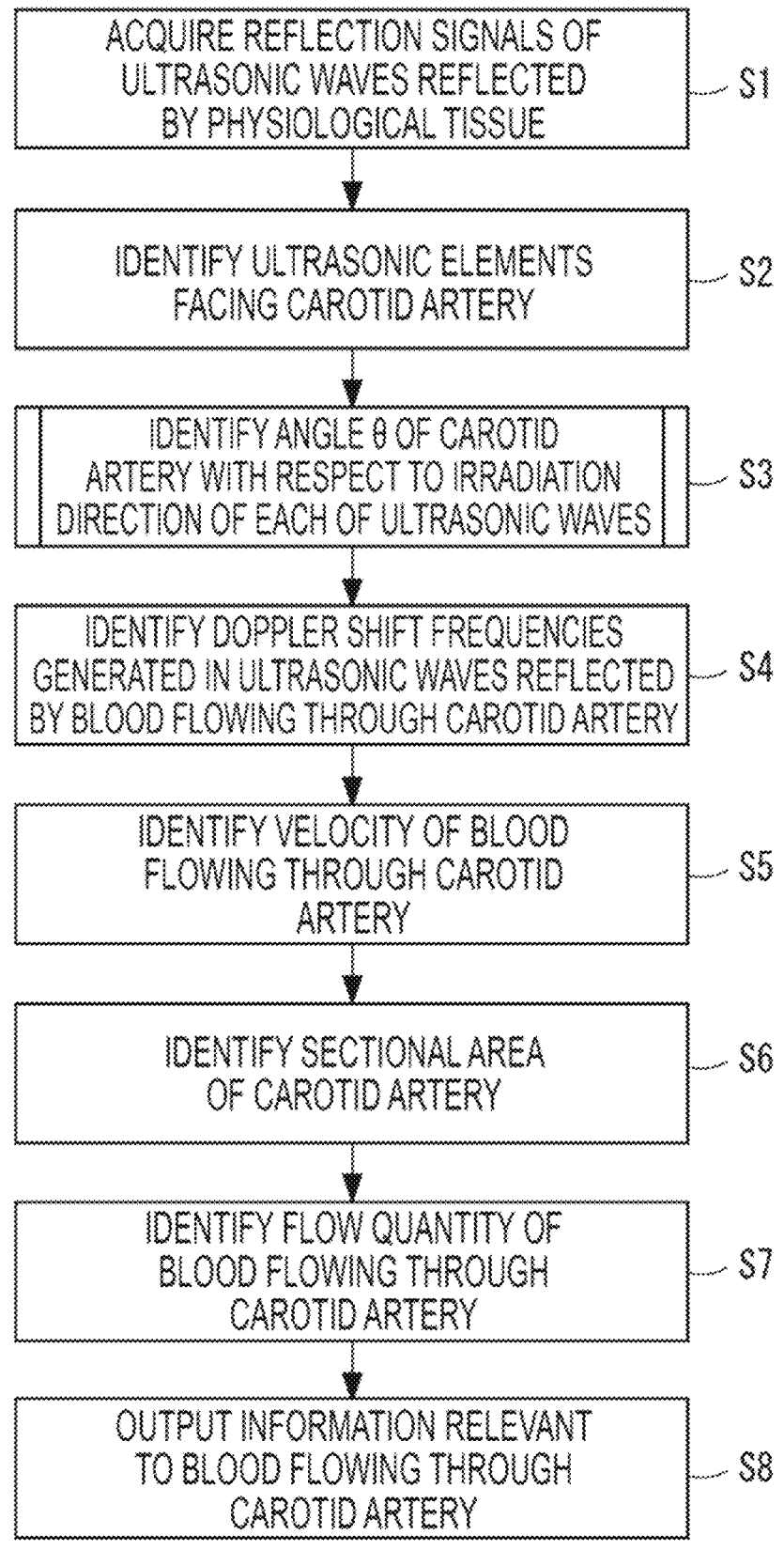

ACQUIRE REFLECTION SIGNALS OF ULTRASONIC WAVES REFLECTED BY PHYSIOLOGICAL TISSUE — S1

IDENTIFY ULTRASONIC ELEMENTS FACING CAROTID ARTERY — S2

IDENTIFY ANGLE θ OF CAROTID ARTERY WITH RESPECT TO IRRADIATION DIRECTION OF EACH OF ULTRASONIC WAVES — S3

IDENTIFY DOPPLER SHIFT FREQUENCIES GENERATED IN ULTRASONIC WAVES REFLECTED BY BLOOD FLOWING THROUGH CAROTID ARTERY — S4

IDENTIFY VELOCITY OF BLOOD FLOWING THROUGH CAROTID ARTERY — S5

IDENTIFY SECTIONAL AREA OF CAROTID ARTERY — S6

IDENTIFY FLOW QUANTITY OF BLOOD FLOWING THROUGH CAROTID ARTERY — S7

OUTPUT INFORMATION RELEVANT TO BLOOD FLOWING THROUGH CAROTID ARTERY — S8

*FIG. 6*

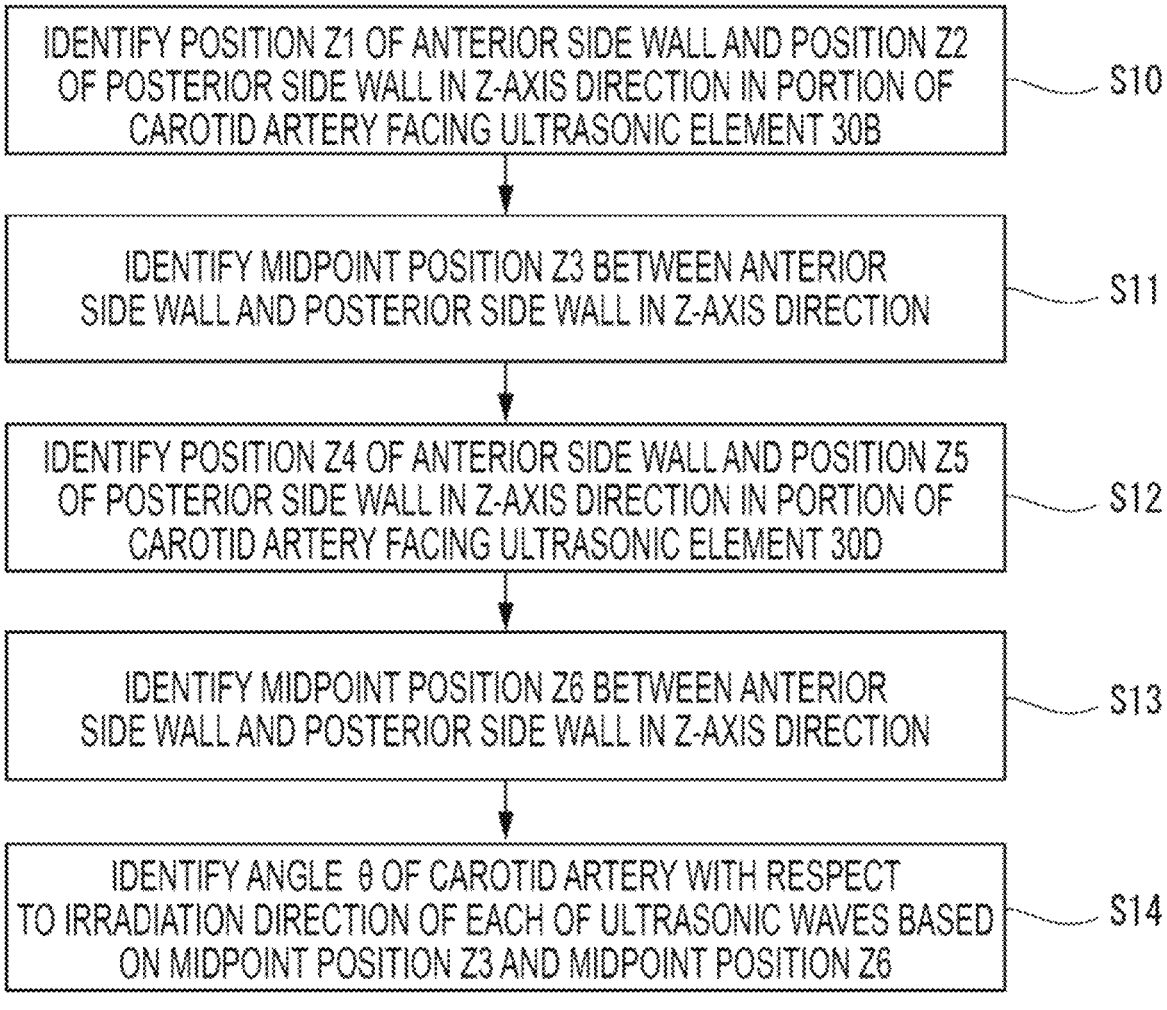

IDENTIFY POSITION Z1 OF ANTERIOR SIDE WALL AND POSITION Z2 OF POSTERIOR SIDE WALL IN Z-AXIS DIRECTION IN PORTION OF CAROTID ARTERY FACING ULTRASONIC ELEMENT 30B — S10

IDENTIFY MIDPOINT POSITION Z3 BETWEEN ANTERIOR SIDE WALL AND POSTERIOR SIDE WALL IN Z-AXIS DIRECTION — S11

IDENTIFY POSITION Z4 OF ANTERIOR SIDE WALL AND POSITION Z5 OF POSTERIOR SIDE WALL IN Z-AXIS DIRECTION IN PORTION OF CAROTID ARTERY FACING ULTRASONIC ELEMENT 30D — S12

IDENTIFY MIDPOINT POSITION Z6 BETWEEN ANTERIOR SIDE WALL AND POSTERIOR SIDE WALL IN Z-AXIS DIRECTION — S13

IDENTIFY ANGLE θ OF CAROTID ARTERY WITH RESPECT TO IRRADIATION DIRECTION OF EACH OF ULTRASONIC WAVES BASED ON MIDPOINT POSITION Z3 AND MIDPOINT POSITION Z6 — S14

PHYSIOLOGICAL INFORMATION PROCESSING METHOD, PHYSIOLOGICAL INFORMATION PROCESSING APPARATUS AND NON-TRANSITORY COMPUTER READABLE STORAGE MEDIUM

CROSS-REFERENCE TO RELATED APPLICATIONS

This application is a National Phase Entry of PCT International Application No. PCT/JP2022/030904 filed on Aug. 15, 2022, which claims priority to Japanese Patent Application No. 2021-134859 filed on Aug. 20, 2021, the entire contents of which are incorporated herein by reference.

TECHNICAL FIELD

The present disclosure relates to a physiological information processing method and a physiological information processing apparatus. In particular, the present disclosure relates to a physiological information processing method and a physiological information processing apparatus using an ultrasonic sensor having a plurality of ultrasonic elements arranged two- dimensionally. Furthermore, the present disclosure relates to a non-transitory computer readable storage medium storing a program for causing a computer to execute the physiological information processing method.

BACKGROUND ART

An ultrasound diagnostic apparatus has currently come into wide use. In the ultrasound diagnostic apparatus, image data indicating a region of interest (ROI) in physiological tissue of a patient is first generated using an ultrasonic sensor provided with a plurality of oscillation elements emitting ultrasonic beams, and then the image data are displayed on a display unit (e.g. see JP-A-2017-86726). The ultrasonic sensor can detect various pieces of information about the physiological tissue of the patient. For example, the ultrasonic sensor can detect velocity of blood flowing through a blood vessel of the patient (blood flow velocity) and a quantity of the blood (blood flow quantity). In this respect, information about the blood flow quantity of a carotid artery may be acquired from the blood flow velocity of the carotid artery using the ultrasonic sensor in order to diagnose a state of the patient's brain. Here, in order to calculate the blood flow velocity of the patient using the ultrasonic sensor, it is necessary to measure a Doppler shift frequency of each ultrasonic wave reflected by red blood cells in the blood. Furthermore, the blood flow velocity can be calculated from the measured Doppler shift frequency in consideration of an angle of the blood vessel with respect to an irradiation direction of the ultrasonic beam.

SUMMARY

In the background art, however, a medical worker determines, by visual observation, the angle of the blood vessel with respect to the irradiation direction of the ultrasonic beam from the ultrasonic image data acquired by the ultrasonic sensor and a set angle of the ultrasonic beam. On the other hand, since the angle of the blood vessel is determined depending on experience or skill of the medical worker, accuracy of the angle of the blood vessel may vary depending on the medical worker in charge. As a result, the accuracy of the finally determined blood flow velocity or blood flow quantity varies depending on the medical worker in charge. Thus, from the aforementioned viewpoint, there is room for study of a method for automatically acquiring information (such as a blood flow quantity of a blood vessel) relevant to a fluid flowing through the body of a subject.

The present disclosure is directed to providing a physiological information processing method and a physiological information processing apparatus that can automatically acquire information relevant to a fluid flowing through the body of a subject.

According to one or more aspects of the present disclosure, there is provided a physiological information processing method for automatically acquiring information relevant to a fluid flowing through a body of a subject using an ultrasonic sensor. The ultrasonic sensor includes a plurality of ultrasonic elements each configured to emit an ultrasonic wave toward a physiological tissue of the subject. The method is performed by a computer and includes: acquiring reflection signals of ultrasonic waves reflected by the physiological tissue; identifying, among the ultrasonic elements, two or more ultrasonic elements facing a vessel through which the fluid flows, based on the reflection signals; analyzing a reflection signal of an ultrasonic wave associated with a first ultrasonic element of the two or more ultrasonic elements to thereby identify a first position of a portion of the vessel facing the first ultrasonic element in an irradiation direction of the ultrasonic wave; analyzing a reflection signal of an ultrasonic wave associated with a second ultrasonic element of the two or more ultrasonic elements to thereby identify a second position of a portion of the vessel facing the second ultrasonic element in the irradiation direction of the ultrasonic wave; identifying an angle of the vessel with respect to the irradiation direction of the ultrasonic wave, based on the first position and the second position; analyzing the reflection signal of the ultrasonic wave associated with the first ultrasonic element or the second ultrasonic element to thereby identify a Doppler shift frequency generated in the ultrasonic wave reflected by the fluid flowing through the vessel; and acquiring information relevant to the fluid at least based on the angle of the vessel and the Doppler shift frequency.

According to the aforementioned method, it is possible to provide a physiological information processing method that can automatically acquire information (such as blood flow velocity or a blood flow quantity) relevant to a fluid (such as blood) flowing through the body of a subject. Thus, the information relevant to the fluid can be automatically acquired. Therefore, accuracy of the information relevant to the fluid can be suitably prevented from varying depending on experience or skill of a medical worker in charge. Furthermore, the information relevant to the fluid is automatically acquired without requiring the medical worker to make any manual operation. Therefore, a workload on the medical worker can be reduced.

According to one or more aspects of the present disclosure, there is provided a physiological information processing apparatus that is configured to automatically acquire information relevant to a fluid flowing through a body of a subject using an ultrasonic sensor. The ultrasonic sensor includes a sheet, and a plurality of ultrasonic elements arranged in a two-dimensional pattern on the sheet and each configured to emit an ultrasonic wave toward a physiological tissue of the subject. The apparatus includes: at least one processor; and a memory that stores a computer-readable instruction that when executed by the processor, causes the apparatus to perform operations includes: acquiring reflection signals of ultrasonic waves reflected by the physiological tissue; identifying, among the ultrasonic elements, two or more ultrasonic elements facing a vessel through which the fluid flows, based on the reflection signals; analyzing a reflection signal of an ultrasonic wave associated with a first ultrasonic element of the two or more ultrasonic elements to thereby identify a first position of a portion of the vessel facing the first ultrasonic element in an irradiation direction of the ultrasonic wave; analyzing a reflection signal of an ultrasonic wave associated with a second ultrasonic element of the two or more ultrasonic elements to thereby identify a second position of a portion of the vessel facing the second ultrasonic element in the irradiation direction of the ultrasonic wave; identifying an angle of the vessel with respect to each of the irradiation direction of the ultrasonic wave, based on the first position and the second position; analyzing the reflection signal of the ultrasonic wave associated with the first ultrasonic element or the second ultrasonic element to thereby identify a Doppler shift frequency generated in the ultrasonic wave reflected by the fluid flowing through the vessel; and acquiring information relevant to the fluid at least based on the angle of the vessel and the Doppler shift frequency.

According to the aforementioned configuration, it is possible to provide a physiological information processing apparatus that can automatically acquire information (such as blood flow velocity or a blood flow quantity) relevant to a fluid (such as blood) flowing through the body of a subject. Thus, the information relevant to the fluid can be automatically acquired. Therefore, accuracy of the information relevant to the fluid can be suitably prevented from varying depending on experience or skill of a medical worker in charge. Furthermore, the information relevant to the fluid can be automatically acquired without requiring the medical worker to make any manual operation. Therefore, a workload on the medical personnel can be reduced.

BRIEF DESCRIPTION OF DRAWINGS

FIG. 4 is a flow chart for explaining a physiological information processing method according to the present embodiment.

FIG. 6 is a flow chart for explaining a process for identifying an angle θ of the carotid artery with respect to an irradiation direction of each of ultrasonic waves.

DESCRIPTION OF EMBODIMENT

Figure 1:
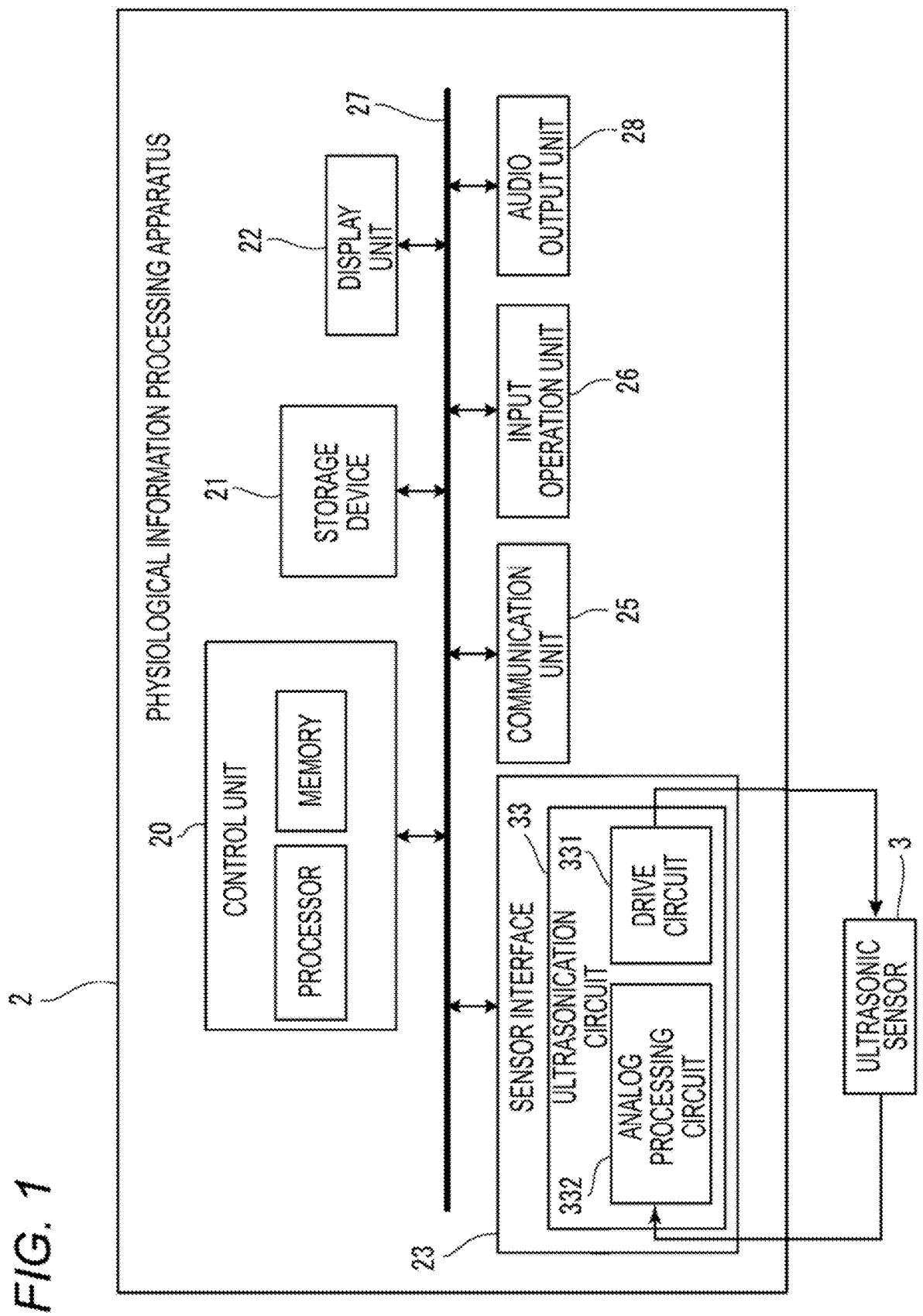
FIG. 1 is a view showing an example of a hardware configuration of a physiological information processing apparatus according to an embodiment of the present disclosure (that will be hereinafter referred to as the "present embodiment").

The present embodiment will be described below with reference to the drawings. First, a hardware configuration of a physiological information processing apparatus 2 (which will be hereinafter simply referred to as "processing apparatus 2") according to the present embodiment will be described with reference to FIG. 1. FIG. 1 is a view showing an example of the hardware configuration of the processing apparatus 2. As shown in FIG. 1, the processing apparatus 2 is provided with a control unit 20, a storage device 21, a communication unit 25, a display unit 22, an audio output unit 28, an input operation unit 26, and a sensor interface 23. These constituent elements are communicably connected to one another through a bus 27. The processing apparatus 2 is electrically connected to an ultrasonic sensor 3.

The processing apparatus 2 may be a medical device (such as a patient monitor) for displaying physiological information of a subject P (see FIG. 3) or may be a personal computer, a workstation, a smartphone, a tablet, or a wearable device (such as AR glasses) worn on the body (such as an arm or the head) of a medical worker.

The control unit 20 is provided with a memory and a processor. The memory is configured so as to store computer-readable instructions (programs). For example, the memory is constituted by an ROM (Read Only Memory) in which various programs etc. have been stored, an RAM (Random Access Memory) having multiple work areas where the various programs executed by the processor are stored, etc. The processor is constituted by, for example, at least one of a CPU (Central Processing Unit), an MPU (Micro Processing Unit) and a GPU (Graphics Processing Unit). The CPU may be composed of a plurality of CPU cores. The GPU may be composed of a plurality of GPU cores. The processor may be configured so as to expand, on the RAM, a program designated from the various programs that have been incorporated into the storage device 21 or the ROM, and execute various processes in cooperation with the RAM. In particular, the processor expands, on the RAM, a physiological information processing program executing a series of processes shown in FIG. 4, and executes the program in cooperation with the RAM. Thus, the control unit 20 executes the series of processes shown in FIG. 4. Details of the physiological information processing program will be described below.

The storage device 21 is a storage device (storage) such as an HDD (Hard Disk Drive), an SSD (Solid State Drive) or a flash memory, which is configured to store the programs and various types of data. The physiological information processing program may be incorporated into the storage device 21. In addition, physiological information data (such as waveform data indicating a change in blood flow quantity and/or blood flow velocity over time) generated based on a physiological signal outputted from the ultrasonic sensor 3 may be stored in the storage device 21.

The communication unit 25 is configured so as to connect the processing apparatus 2 to an intrahospital network. Specifically, the communication unit 25 may include various wired connection terminals for communication with a central monitor or a server disposed in the intrahospital network. In addition, the communication unit 25 may include a wireless communication module for wireless communication with the central monitor or the server. The communication unit 25 may include, for example, a wireless communication module compatible with a medical telemetry system. Moreover, the communication unit 25 may include a wireless communication module compatible with any of wireless communication standards such as Wi-Fi (registered trademark) and Bluetooth (registered trademark) and/or a wireless communication module compatible with a mobile communication system using SIM. The intrahospital network may be composed of, for example, an LAN (Local Area Network) or a WAN (Wide Area Network). The processing apparatus 2 may be connected to the Internet through the intrahospital network.

The display unit 22 is configured so as to display information that has been acquired in real time to be relevant to blood flowing through a carotid artery of the subject P. For example, the display unit 22 is constituted by a liquid crystal panel or an organic EL panel. The audio output unit 28 is constituted by one or more speakers and configured so as to audibly output an audio alert in accordance with the information relevant to the blood flowing through the carotid artery of the subject P. The input operation unit 26 is, for example, a touch panel disposed to be superimposed on the display unit 22, a mouse, and/or a keyboard etc. The input operation unit 26 is configured so as to accept an input operation made by a medical worker and generate an operation signal corresponding to the input operation made by the medical worker. After the operation signal generated by the input operation unit 26 is transmitted to the control unit 20 through the bus 27, the control unit 20 executes a predetermined action in response to the operation signal.

Figure 2:
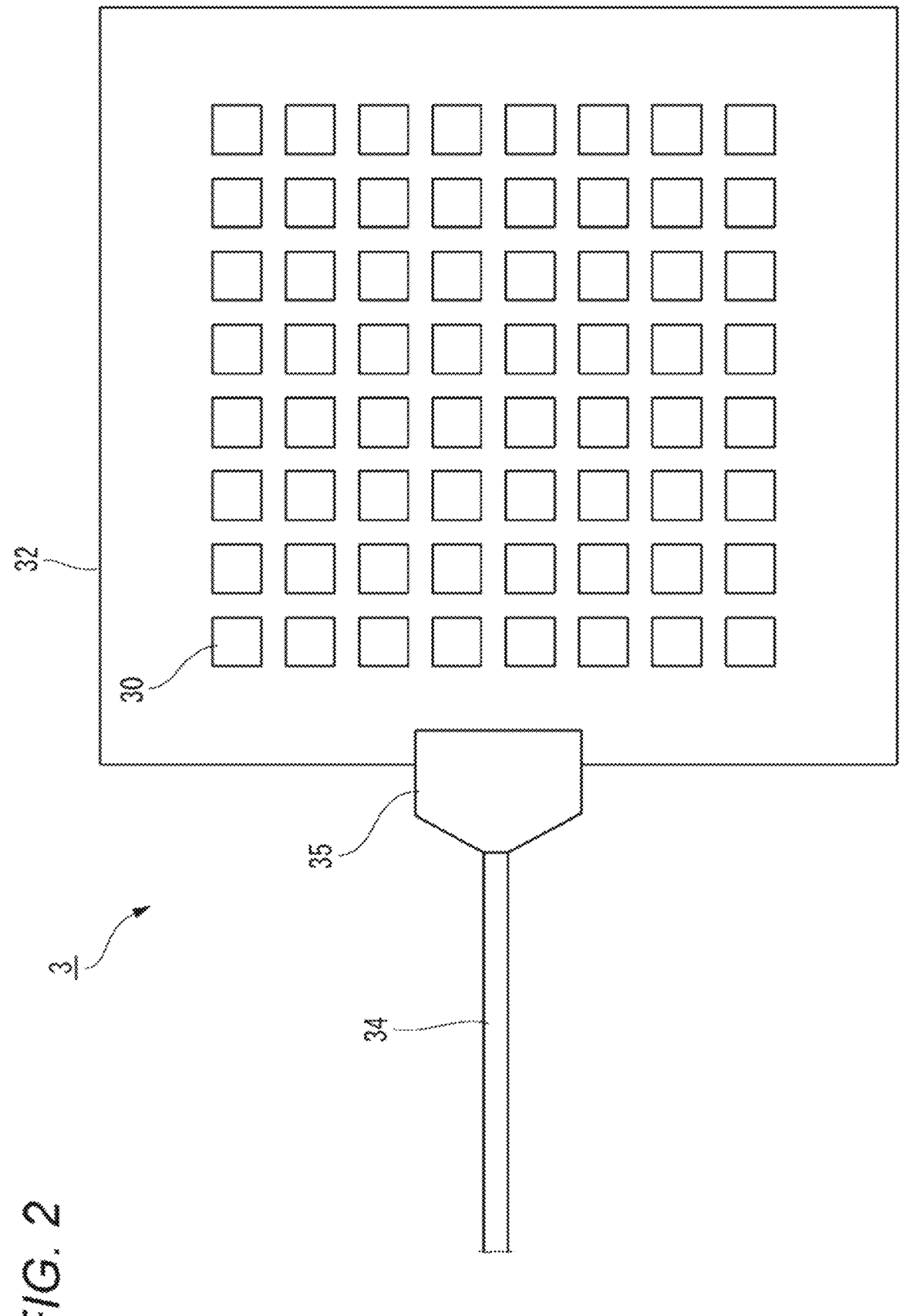
FIG. 2 is a plan view schematically showing an example of an ultrasonic sensor.

The ultrasonic sensor 3 is configured so as to emit ultrasonic waves toward physiological tissue of the subject to thereby detect information relevant to the physiological tissue of the subject (the information relevant to the blood flowing through the carotid artery in the present example). As shown in FIG. 2, the ultrasonic sensor 3 is provided with a sheet 32, a plurality of ultrasonic elements 30, a sheet fixing unit 35 and a connection cable 34. The ultrasonic sensor 3 may be a disposable sensor. The sheet 32 is pasted on a predetermined region (a neck portion in the present example) of the subject P (see FIG. 3). The sheet 32 is, for example, made of a flexible material such as silicone.

The plurality of ultrasonic elements 30 are arranged in a two-dimensional pattern on one face of the sheet 32. In the present example, the plurality of ultrasonic elements 30 are arranged in a matrix pattern with eight rows and eight columns. A distance between the ultrasonic elements 30 adjacent to each other in the row and column directions may be approximately constant. Each of the ultrasonic elements 30 is configured so as to transmit an ultrasonic wave toward the physiological tissue of the subject P, and configured so as to receive the ultrasonic wave reflected by the physiological tissue. In particular, the ultrasonic element 30 is configured so as to oscillate in response to an electrical drive signal (high-frequency signal) transmitted from a drive circuit 331 which will be described later, to thereby transmit an ultrasonic wave, and to convert the ultrasonic wave reflected by the physiological tissue into an electrical signal. After the ultrasonic wave is outputted from the ultrasonic element 30, a reflection signal of the ultrasonic wave reflected by the physiological tissue is inputted to the sensor interface 23 through the sheet fixing unit 35 and the connection cable 34. In addition, in the present embodiment, the ultrasonic element 30 may output ultrasonic wave pulses with a predetermined frequency (e.g. 8 kHz).

The sensor interface 23 is an interface for communicably connecting the ultrasonic sensor 3 to the processing apparatus 2. The sensor interface 23 may include an input terminal through which a physiological signal outputted from the ultrasonic sensor 3 is input to the processing apparatus 2. The input terminal may be physically connected to a connector of the ultrasonic sensor 3. In addition, the sensor interface 23 may include an ultrasonication circuit 33. The ultrasonication circuit 33 includes the drive circuit 331 and an analog processing circuit 332. The drive circuit 331 is provided with an oscillation circuit. The drive circuit 331 is configured to generate a drive signal for driving the ultrasonic elements 30 of the ultrasonic sensor 3 and then transmit the drive signal to each of the ultrasonic elements

30. The analog processing circuit 332 is configured so as to apply signal processing to the reflection signal of the ultrasonic wave outputted from the ultrasonic element 30. The analog processing circuit 332 includes, for example, at least a filter processing circuit for removing a noise component from the reflection signal outputted from the ultrasonic element 30, a signal amplification circuit that amplifies the reflection signal, and an AD conversion circuit that converts the reflection signal from an analog signal into a digital signal. Thus, the analog reflection signal of the ultrasonic wave outputted from the ultrasonic sensor 3 is converted into a digital reflection signal of an ultrasonic wave by the sensor interface 23, and then the digital reflection signal is transmitted to the control unit 20.

Figure 3:
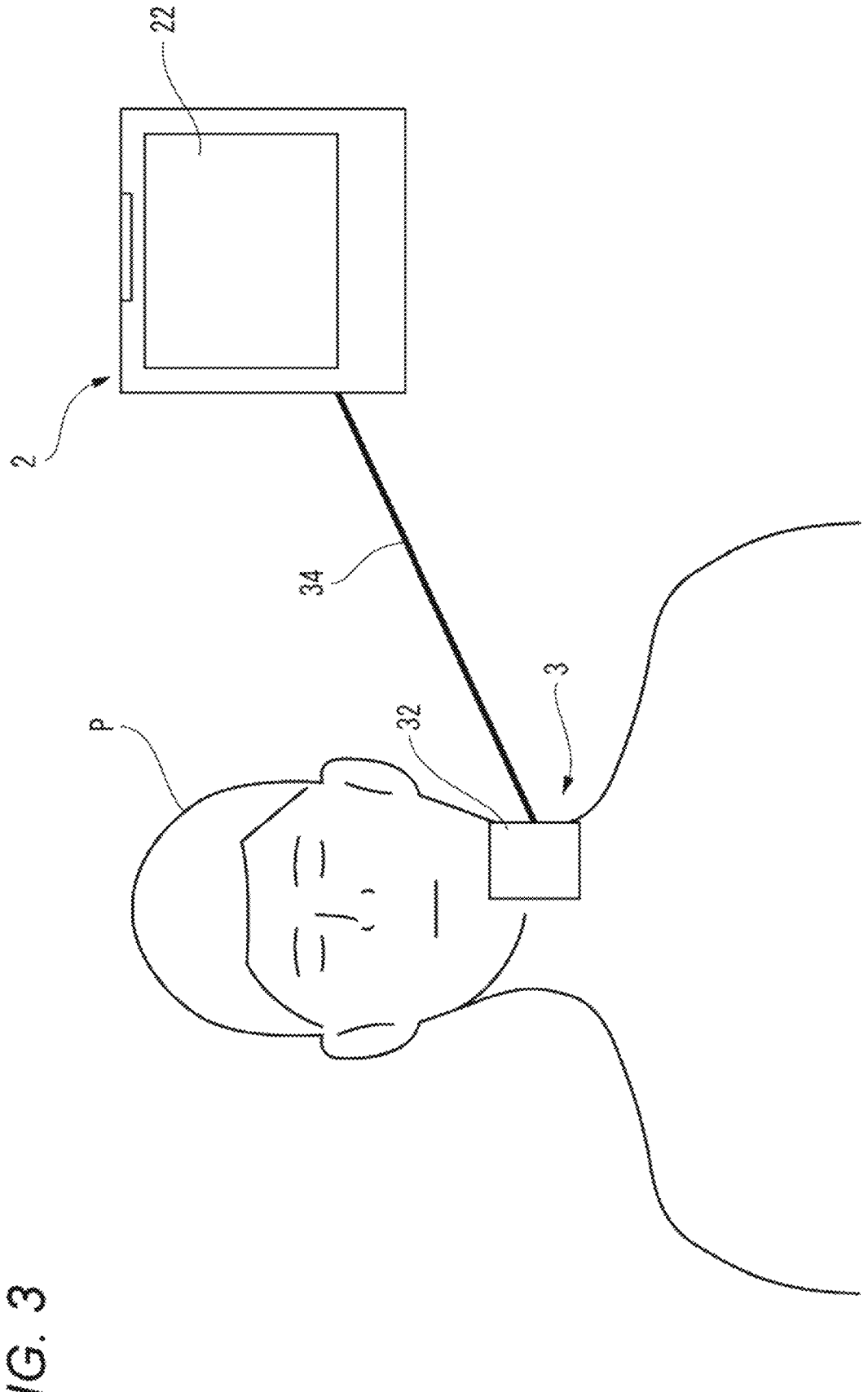
FIG. 3 is a view showing a state in which the ultrasonic sensor has been attached to a neck portion of a subject.
Figure 5:
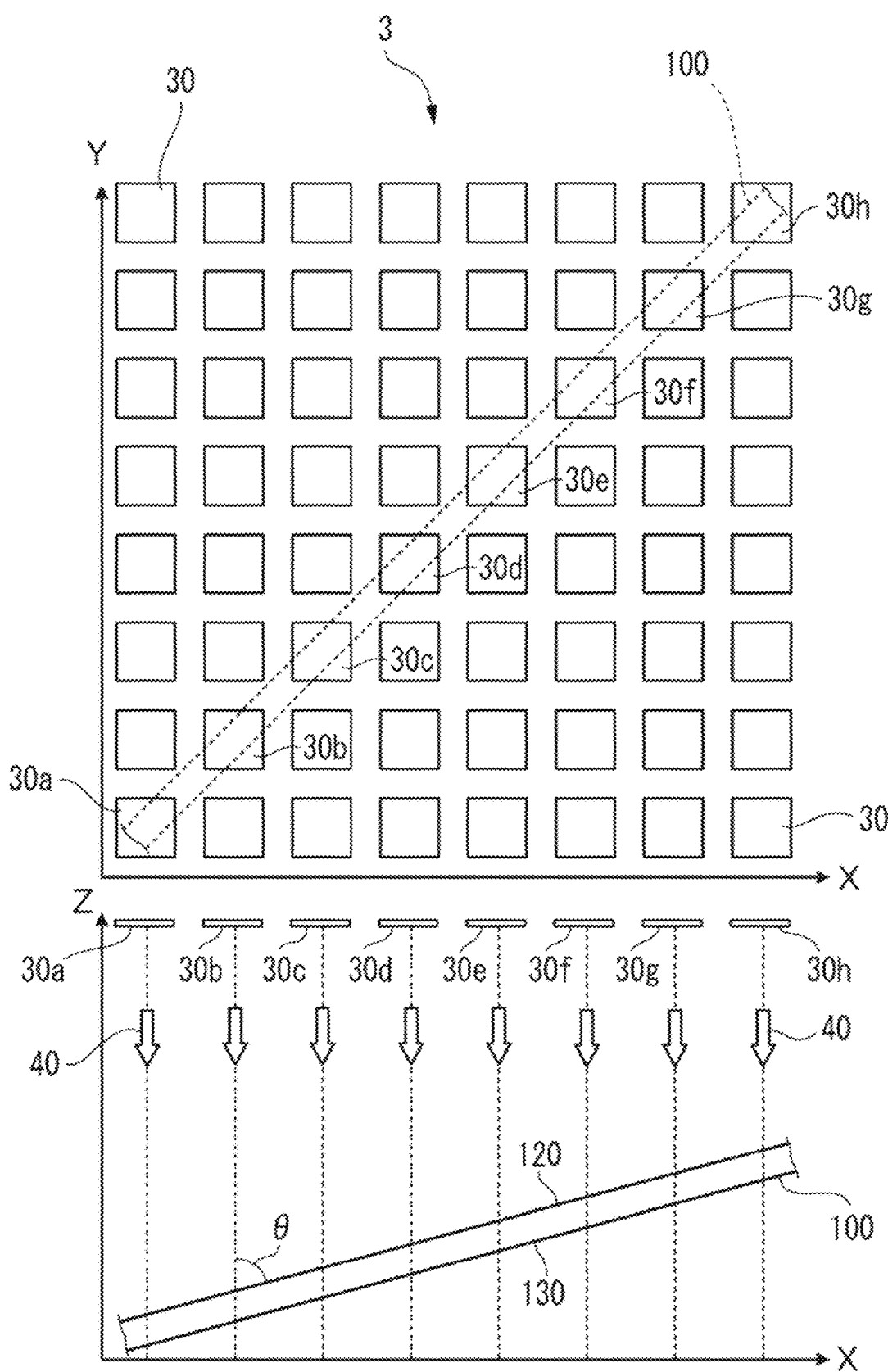
FIG. 5 is a view showing a state in which each of ultrasonic elements provided in the ultrasonic sensor faces a carotid artery of the subject.

Next, a physiological information processing method (in particular, a series of processes for acquiring the information relevant to the blood flowing through the carotid artery of the subject P) according to the present embodiment will be described below, mainly with reference to FIG. 4. FIG. 4 is a flowchart for explaining the physiological information processing method according to the present embodiment. Incidentally, in the following description, X-axis, Y-axis, and Z-axis directions set relatively on the ultrasonic sensor 3 will be referred to, as shown in FIG. 5. One of the X-axis, Y-axis, and Z-axis directions is orthogonal to the other two directions. The plurality of ultrasonic elements 30 are arranged in a two-dimensional pattern in an XY plane. The sheet 32 of the ultrasonic sensor 3 is pasted on the neck portion of the subject P, as shown in FIG. 3, and parts of the plurality of ultrasonic elements 30 face the carotid artery 100 (an example of a blood vessel) of the subject P in the Z-axis direction perpendicular to the XY plane. An irradiation direction of an ultrasonic beam emitted from each of the ultrasonic elements 30 is parallel to the Z-axis direction.

In a step S1, as shown in FIG. 4, the control unit 20 of the processing apparatus 2 acquires reflection signals (digital signals) of ultrasonic waves 40 reflected by the physiological tissue of the subject P, from the ultrasonic sensor 3 through the ultrasonication circuit 33 (the step S1). In particular, the control unit 20 acquires the reflection signals of the ultrasonic waves 40 outputted from ones of the ultrasonic elements 30.

In a step S2, the control unit 20 identifies the ultrasonic elements 30 facing the carotid artery 100 of the subject P in the Z-axis direction based on the reflection signals of the ultrasonic waves. As shown in FIG. 5, of the ultrasonic elements 30, ultrasonic elements 30a to 30h face the carotid artery 100 in the Z-axis direction in the present example.

In this respect, the control unit 20 identifies the ultrasonic elements 30a to 30h facing the carotid artery 100 in the Z-axis direction based on components of the reflection signals of the ultrasonic waves 40. In general, the ultrasonic waves are reflected at a boundary between media different in acoustic characteristic impedance. Therefore, the ultrasonic waves are reflected at the boundary between the carotid artery 100 and the physiological tissue adjacent to the carotid artery 100. In particular, due to a large difference in the acoustic characteristic impedance between the carotid artery 100 and the physiological tissue adjacent to the carotid artery 100, the ultrasonic waves 40 are respectively intensely reflected on an anterior side wall 120 and a posterior side wall 130 of the carotid artery 100. In addition, patterns of the components of the reflection signals of the ultrasonic waves 40 reflected by the anterior side wall 120 and the posterior side wall 130 of the carotid artery 100 have been found out in advance. Here, the control unit 20 can determine the ultrasonic elements 30 associated with the reflection signals having predetermined reflection signal components (e.g. reflection signal components C1, C2, etc. shown in FIG. 7) as the ultrasonic elements facing the carotid artery 100 in the Z-axis direction.

Figure 7:
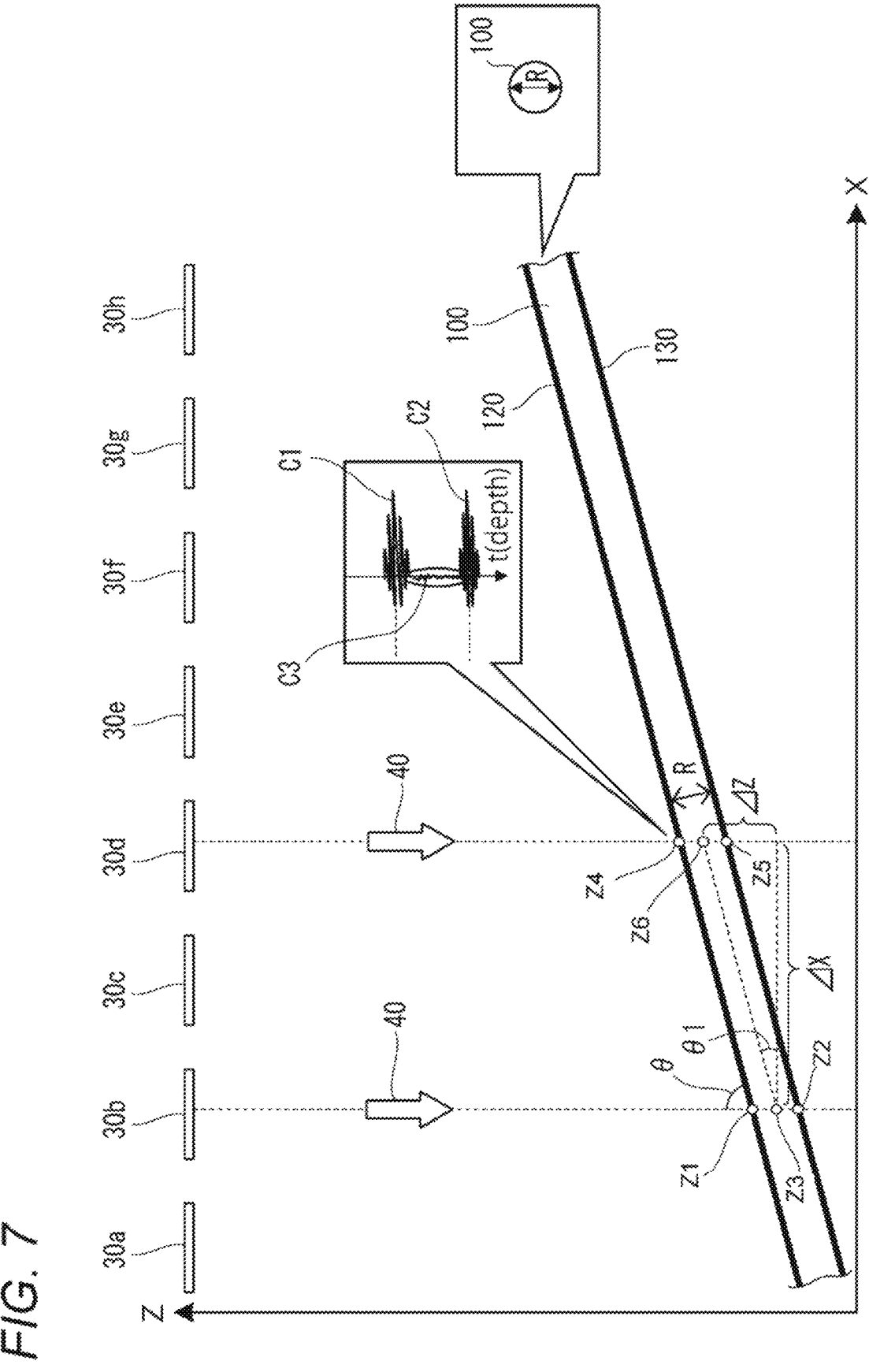
FIG. 7 is a view for explaining midpoint positions between an anterior side wall and a posterior side wall of the carotid artery in a Z-axis direction.

Next, in a step S3, the control unit 20 identifies an angle 0 of the carotid artery 100 with respect to the irradiation direction (the Z-axis direction) of each of the ultrasonic waves 40 (ultrasonic beams). A specific process of the step S3 will be described below in detail with reference to FIG. 6 and FIG. 7. FIG. 6 shows a flow chart for explaining the process for identifying the angle θ of the carotid artery 100 with respect to the irradiation direction (the Z-axis direction) of the ultrasonic wave 40. FIG. 7 shows a view for explaining midpoint positions Z3 and Z6 between the anterior side wall 120 and the posterior side wall 130 of the carotid artery 100 in the Z-axis direction. Incidentally, in the following description, the angle θ of the carotid artery 100 with respect to the Z-axis direction is identified based on the reflection signals of the ultrasonic waves 40 transmitted from two ultrasonic elements 30b and 30d of the ultrasonic elements 30a to 30h facing the carotid artery 100. In addition, thickness of each of the walls of the carotid artery 100 is sufficiently small.

As shown in FIG. 6, in a step S10, the control unit 20 analyzes the reflection signal of the ultrasonic wave 40 transmitted from the ultrasonic element 30b (an example of a first ultrasonic element), to thereby identify a position Z1 of the anterior side wall 120 and a position Z2 of the posterior side wall 130 in the Z-axis direction in a portion of the carotid artery 100 facing the ultrasonic element 30b. Specifically, the control unit 20 analyzes the reflection signal of the ultrasonic wave 40 transmitted from the ultrasonic element 30b to thereby identify a component of the reflection signal of the ultrasonic wave 40 reflected by the anterior side wall 120. Next, the control unit 20 identifies a time instant of reception of the component of the reflection signal of the ultrasonic wave 40 reflected by the anterior side wall 120. Then, the control unit 20 identifies a distance L1 between the ultrasonic element 30b and the anterior side wall 120 in the Z-axis direction based on a time instant t0 of the transmission of the ultrasonic wave 40 and the time instant t1 of the reception of the component of the reflection signal of the ultrasonic wave 40 reflected by the anterior side wall 120. Here, the distance L1=c(t1−t0)/2, wherein c is sound velocity of the ultrasonic wave 40 traveling through the physiological tissue. Thus, the control unit 20 can identify the position Z1 of the anterior side wall 120 in the Z-axis direction.

In a similar manner or the same manner, the control unit 20 analyzes the reflection signal of the ultrasonic wave 40 transmitted from the ultrasonic element 30b, to thereby identify a component of the reflection signal of the ultrasonic wave 40 reflected by the posterior side wall 130. Next, the control unit 20 identifies a time instant of reception of the component of the reflection signal of the ultrasonic wave 40 reflected by the posterior side wall 130. Then, the control unit 20 identifies a distance L2 (L2=c(t2−t0)/2) between the ultrasonic element 30b and the posterior side wall 130 in the Z-axis direction based on the time instant to of the transmission of the ultrasonic wave 40 and the time instant t2 of the reception of the component of the reflection signal of the ultrasonic wave 40 reflected by the posterior side wall 130. Thus, the control unit 20 can identify the position Z2 of the posterior side wall 130 in the Z-axis direction.

Next, in a step S11, the control unit 20 identifies a midpoint position Z3 (Z3=(Z1+Z2)/2) between the position Z1 of the anterior side wall 120 and the position Z2 of the posterior side wall 130 in the Z-axis direction.

In a step S12, the control unit 20 analyzes the reflection signal of the ultrasonic wave 40 transmitted from the ultrasonic element 30d (an example of a second ultrasonic element), to thereby identify a position Z4 of the anterior side wall 120 and a position Z5 of the posterior side wall 130 in the Z-axis direction in a portion of the carotid artery 100 facing the ultrasonic element 30d. Specifically, the control unit 20 analyzes the reflection signal of the ultrasonic wave 40 transmitted from the ultrasonic element 30d to thereby identify a component C1 (see FIG. 7) of the reflection signal of the ultrasonic wave 40 reflected by the anterior side wall 120. Next, the control unit 20 identifies a time instant of reception of the component C1 of the reflection signal of the ultrasonic wave 40 reflected by the anterior side wall 120. Then, the control unit 20 identifies a distance between the ultrasonic element 30d and the anterior side wall 120 in the Z-axis direction based on a time instant of the transmission of the ultrasonic wave 40 and the time instant of the reception of the component C1 of the reflection signal of the ultrasonic wave 40 reflected by the anterior side wall 120. Thus, the control unit 20 can identify the position Z4 of the anterior side wall 120 in the Z-axis direction.

In a similar manner or the same manner, the control unit 20 analyzes the reflection signal of the ultrasonic wave 40 transmitted from the ultrasonic element 30d, to thereby identify a component C2 (see FIG. 7) of the reflection signal of the ultrasonic wave 40 reflected by the posterior side wall 130. Next, the control unit 20 identifies a time instant of reception of the component C2 of the reflection signal of the ultrasonic wave 40 reflected by the posterior side wall 130. Then, the control unit 20 identifies a distance between the ultrasonic element 30d and the posterior side wall 130 in the Z-axis direction based on the time instant of the transmission of the ultrasonic wave 40 and the time instant of the reception of the component C2 of the reflection signal of the ultrasonic wave 40 reflected by the posterior side wall 130. Thus, the control unit 20 can identify the position Z5 of the posterior side wall 130 in the Z-axis direction.

Next, in a step S13, the control unit 20 identifies a midpoint position Z6 (Z6=(Z4+Z5)/2) between the position Z4 of the anterior side wall 120 and the position Z5 of the posterior side wall 130 in the Z-axis direction.

In a step S14, the control unit 20 identifies an angle θ of the carotid artery 100 with respect to the irradiation direction of each of the ultrasonic waves 40 based on the midpoint position Z3 and the midpoint position Z6. Specifically, as shown in FIG. 7, the control unit 20 identifies an angle θ1 of the carotid artery 100 with respect to the X-axis direction based on a distance ΔZ between the position Z6 and the position Z3 in the Z-axis direction and a distance ΔX between the ultrasonic element 30b and the ultrasonic element 30d in the X-axis direction. More specifically, the angle θ1 is calculated according to a relational expression θ1=tan−1 (ΔZ/ΔX). In addition, due to the relational expression of the angle θ=(90°−θ1), the control unit 20 can identify the angle θ of the carotid artery 100 with respect to the Z-axis direction from the calculated angle θ1.

Incidentally, the distance AX may be a distance between a center position of the ultrasonic element 30b and a center position of the ultrasonic element 30d in the X-axis direction. In addition, in the present example, the angle θ of the carotid artery 100 is identified based on the reflection signals of the ultrasonic waves 40 transmitted from the ultrasonic elements 30b and 30d. However, the present embodiment is not limited thereto. For example, the angle θ of the carotid artery 100 may be identified based on the reflection signals of the ultrasonic waves 40 transmitted from the ultrasonic elements 30*b* and 30*c* or the ultrasonic elements 30*c* and 30*d* or the angle θ of the carotid artery 100 may be identified based on the reflection signals of the ultrasonic waves 40 transmitted from any two ultrasonic elements of the ultrasonic elements 30*a* to 30*h* facing the carotid artery 100.

Moreover, in the present example, the angle θ of the carotid artery 100 is determined based on the distance between the two midpoint positions Z3 and Z6. However, the present embodiment is not limited thereto. For example, the angleθ of the carotid artery 100 may be determined based on a distance between the positions Z1 and Z4 of the anterior side wall 120 in the X-axis direction, or the angle θ of the carotid artery 100 may be determined based on a distance between the positions Z2 and Z5 of the posterior side wall 130.

Refer to FIG. 4. In a step S4, the control unit 20 identifies Doppler shift frequencies fd generated in the ultrasonic waves 40 reflected by the blood flowing through the carotid artery 100. In this respect, the control unit 20 may analyze reflection signals of ultrasonic waves 40 transmitted from one or more ultrasonic elements of the ultrasonic elements 30*a* to 30*h* facing the carotid artery 100, to thereby identify Doppler shift frequencies fd generated in the ultrasonic waves reflected by the blood (more specifically, red blood cells).

When velocity of the blood flowing through the carotid artery 100 (blood flow velocity) is v, the red blood cells contained in the blood also move through the carotid artery 100 at the velocity v. Moreover, when the angle of the carotid artery 100 with respect to the Z-axis direction is θ, the red blood cells are observed as if they are moving in the Z-axis direction at a velocity v*cosθ. In addition, after the ultrasonic waves 40 transmitted from the ultrasonic elements 30 and passing through the carotid artery 100 are reflected by the red blood cells moving in the Z-axis direction at the velocity v*cosθ, a corresponding one of the ultrasonic waves 40 is received by the ultrasound element 30*b*. Thus, the frequency of the ultrasonic wave 40 reflected by the red blood cells moving in the Z-axis direction at the velocity v*cosθ varies due to the Doppler effect.

Here, when the frequency of the ultrasonic wave 40 transmitted from each of the ultrasound elements 30 is f0, the Doppler shift frequency is fd, the velocity of the blood flowing through the carotid artery 100 is v, the angle of the carotid artery 100 with respect to the Z-axis direction is 0, and the sound velocity of the ultrasonic wave travelling through the physiological tissue is c, the Doppler shift frequency fd is derived by the following expression (1).

$$fd = 2vf0 \times \cos\theta/c \qquad (1)$$

From the aforementioned expression (1), it is understood that the Doppler shift frequency fd varies in proportion to the velocity v of the blood flowing through the carotid artery 100. In other words, when the Doppler shift frequency fd is measured, the blood flow velocity v in the carotid artery 100 can be measured.

The control unit 20 can, for example, analyze the reflection signal of the ultrasonic wave 40 associated with at least one of the ultrasonic elements 30*a* to 30*h* by a pulsed Doppler method or a color Doppler method, to thereby identify the Doppler shift frequency fd. For example, assume that the Doppler shift frequency fd is identified by the pulsed Doppler method. In this case, after acquiring data indicating a change in the sum of luminance values of a component C3 (see FIG. 7) of the reflection signal of the ultrasonic wave reflected by the red blood cells in the carotid artery 100 with respect to each ultrasonic wave pulse, the control unit 20 can execute Fast Fourier Transform (FFT) on the acquired data to thereby identify the Doppler shift frequency fd. On the other hand, assume that the Doppler shift frequency fd is identified by the color Doppler method. In this case, the control unit 20 can estimate the Doppler shift frequency fd by an autocorrelation method. In addition, when the frequency of the ultrasonic wave is 8 kHz (in other words, when 8000 ultrasonic wave pulses are outputted per second), the control unit 20 may calculate the Doppler shift frequency fd every 140 ultrasonic wave pulses. In this case, an update rate of the Doppler shift frequency fd is 57 Hz.

In addition, a computational load caused by the FFT in the pulsed Doppler method is larger. Therefore, a computational load on the control unit 20 for computational processing through the color Doppler method is advantageously smaller than a computational load on the control unit 20 for computational processing through the pulsed Doppler method.

Next, in a step S5, the control unit 20 identifies the velocity (blood flow velocity) v of the blood flowing through the carotid artery 100. In this respect, the aforementioned expression (1) can be rearranged as follows.

$$v = (cfd)/(2f0 \cos\theta) \qquad (2)$$

Based on the aforementioned expression (2), the control unit 20 can calculate the blood flow velocity v from the Doppler shift frequency fd, the frequency f0, the angle θ of the carotid artery 100 and the sound velocity c.

Next, in a step S6, the control unit 20 identifies a sectional area S of the carotid artery 100. Here, the sectional area S of the carotid artery 100 that is a sectional area perpendicular to an axial direction of the carotid artery 100 means a sectional area of a hollow portion of the carotid artery 100, through which the blood flows. Here, when an internal diameter of the carotid artery 100 is R, the sectional area S of the carotid artery 100 establishes a relational expression S=πR2/4. Moreover, when a distance between the position Z1 and the position Z2 is |Z1–Z2|, as shown in FIG. 7, the internal diameter R can be calculated according to a relational expression R=|Z1–Z2|sinθ. In a similar manner or the same manner, when a distance between the position Z4 and the position Z5 is |Z4–Z5|, the internal diameter R can be calculated according to a relational expression R=|Z4–Z5|sinθ. Incidentally, as described above, thickness of each of the walls of the carotid artery 100 is assumed to be sufficiently small.

A case where the sectional area S of the carotid artery 100 is calculated based on the reflection signal of the ultrasonic wave associated with the ultrasound element 30*b* will be described below briefly. In this case, first, the control unit 20 analyzes the reflection signal of the ultrasonic wave associated with the ultrasound element 30*b* to thereby identify the position Z1 of the anterior side wall 120 and the position Z2 of the posterior side wall 130 in the Z-axis direction. Next, the control unit 20 identifies the distance |Z1–Z2| between the position Z1 of the anterior side wall 120 and the position Z2 of the posterior side wall 130. Then, based on the relational expression R=|Z1–Z2|sinθ, the control unit 20 identifies the internal diameter R of the carotid artery 100 from the angle θ of the carotid artery 100 and the distance

|Z1−Z2|. Finally, the control unit 20 identifies the sectional area S of the carotid artery 100 from the internal diameter R of the carotid artery 100 according to the relational expression S=πR2/4. Incidentally, the sectional area S of the carotid artery 100 may be calculated based on a reflection signal of an ultrasonic wave associated with at least one of the ultrasonic elements 30*a* to 30*h* facing the carotid artery 100.

Next, in a step S7, the control unit 20 identifies a flow quantity (blood flow quantity) Q of the blood flowing through the carotid artery 100. Here, the blood flow quantity Q establishes a relation expression Q=Sv (v is the blood flow velocity and S is the sectional area of the carotid artery 100). Thus, the control unit 20 can identify the blood flow quantity Q of the carotid artery 100 based on the calculated blood flow velocity v and the calculated sectional area S of the carotid artery 100.

In a step S8, the control unit 20 outputs information relevant to the blood flowing through the carotid artery 100. For example, the control unit 20 may display, on a display screen of the display unit 22, waveform data indicating a change in the blood flow quantity Q of the carotid artery 100 over time and/or waveform data indicating a change in the blood flow velocity v of the carotid artery 100 over time. In this case, the medical worker can view the waveform data displayed on the display unit 22 to thereby accurately grasp symptoms of the subject P. In particular, the medical worker can observe the change in the blood flow quantity Q or the blood flow velocity v of the carotid artery 100 over time to thereby accurately grasp a state of the brain of the subject P (in particular, a supply state of the blood flowing to the brain).

In addition, after determining whether the blood flow quantity Q of the carotid artery 100 is equal to or smaller than a predetermined threshold Qth or not, the control unit 20 may audibly output an alert from the audio output unit 28 in accordance with the determination that the blood flow quantity Q of the carotid artery 100 is equal to or smaller than the predetermined threshold Qth. After determining whether the blood flow velocity v of the carotid artery 100 is equal to or smaller than a predetermined threshold vth or not, the control unit 20 may likewise audibly output an alert from the audio output unit 28 in accordance with the determination that the blood flow velocity v of the carotid artery 100 is equal to or smaller than the predetermined threshold vth.

In this case, the medical worker can instantaneously grasp a change in the state of the brain of the subject P (in particular, the supply state of the blood flowing to the brain) when hearing the alert outputted from the audio output unit 28 of the processing apparatus 2. In addition, the control unit 20 may display a warning indication on the display screen of the display unit 22 in response to determining that the blood flow quantity Q or the blood flow velocity v of the carotid artery 100 is equal to or smaller than the predetermined threshold. Even in this case, the medical worker can likewise instantaneously grasp the change in the state of the brain of the subject P when viewing the warning indication displayed on the display unit 22. Further, the control unit 20 may store, in the storage device 21, the waveform data indicating the change in the blood flow quantity Q or the blood flow velocity v over time, or may transmit the waveform data to the central monitor or the server provided on the intrahospital network through the communication unit 25.

Incidentally, in the aforementioned description, the control unit 20 audibly or visually presents the warning to the medical worker in response to determining that the blood flow quantity Q or the blood flow velocity v of the carotid artery 100 is equal to or smaller than the predetermined threshold. However, the present embodiment is not limited thereto. For example, the control unit 20 may audibly or visually present the warning to the medical worker in response to determining that a variation width of the blood flow quantity Q or the blood flow velocity v is equal to or smaller than a predetermined threshold. Here, the "variation width of the blood flow quantity Q or the blood flow velocity v" corresponds to a difference between a current blood flow quantity Q or a current blood flow velocity v and a blood flow quantity Q or a blood flow velocity v a predetermined time before.

In addition, in the present embodiment, the information relevant to the blood flowing through the carotid artery 100 is acquired based on the reflection signals of the ultrasonic waves associated with the ultrasonic elements 30*a* to 30*h* facing the carotid artery 100. Therefore, after the ultrasonic elements 30*a* to 30*h* facing the carotid artery 100 are identified in the step S2, only the ultrasonic elements 30*a* to 30*h* may be driven. That is, the drive circuit 331 may supply a drive signal to only the ultrasonic elements 30*a* to 30*h*. In this case, only the ultrasonic elements 30*a* to 30*h* are driven. Therefore, an irradiation quantity of the ultrasonic waves with which the physiological tissue of the subject P is irradiated can be reduced. Thus, an impact on the physiological tissue of the subject P due to the irradiation with the ultrasonic waves can be suppressed as much as possible, and power consumption of the ultrasonic sensor 3 can be reduced.

According to the present embodiment, as described above, it is possible to provide the processing apparatus 2 that can automatically acquire blood flow information relevant to the blood flowing through the carotid artery 100 (such as the waveform data indicating the change in the blood flow velocity v or the blood flow quantity Q over time) without requiring the medical worker to make any manual operation. Since the blood flow information is automatically acquired thus, accuracy of the blood flow information can be suitably prevented from varying depending on experience or skill of the medical worker in charge. Furthermore, since the blood flow information is automatically acquired without requiring the medical worker to make any manual operation, a workload on the medical worker can be reduced. In particular, in comparison with the background-art ultrasound diagnostic method, the angle θ of the carotid artery 100 with respect to the irradiation direction of the ultrasonic beams and the sectional area S perpendicular to the axial direction of the carotid artery 100 are automatically determined by the processing apparatus 2. Therefore, the accuracy of the blood flow information can be improved and the workload on the medical worker can be reduced.

Moreover, in order to realize the processing apparatus 2 according to the present embodiment by software, a physiological information processing program may be incorporated into the storage device 21 or the ROM in advance. Alternatively, the physiological information processing program may be stored in a computer-readable storage medium such as a magnetic disk (such as an HDD or a floppy disk), an optical disk (such as a CD-ROM, a DVD-ROM or a Blu-ray (registered trademark) disk), a magneto-optical disk (such as an MO), a flash memory (such as an SD card, a USB memory or an SSD). In this case, the physiological information processing program that has been stored in the storage medium may be incorporated into the storage device 21. Further, after the program that has been incorporated into the storage device 21 is loaded onto the RAM, the processor may execute the program loaded on the RAM. In this manner, the physiological information processing method according to the present embodiment is executed by the processing apparatus 2. Moreover, the physiological information processing program may be downloaded from a computer on a communication network through the communication unit 25. Even in this case, the downloaded program may be incorporated into the storage device 21 in a similar manner or the same manner.

For example, in the description of the present embodiment, the information relevant to the blood flowing through the carotid artery is automatically acquired by the processing apparatus 2. However, the blood vessel is not limited to the carotid artery. For example, information relevant to blood flowing through another blood vessel than the carotid artery may be alternatively automatically acquired by the processing apparatus 2.

Furthermore, the flow quantity or velocity of the blood is automatically acquired by the processing apparatus 2 in the present embodiment. However, the processing apparatus 2 may alternatively automatically acquire information relevant to another fluid flowing through the body of the subject than the blood. For example, the processing apparatus 2 may alternatively automatically acquire a flow quantity or velocity of urine flowing through the ureter as another example of the vessel of the subject. In this case, the sheet 32 of the ultrasonic sensor 3 is pasted onto the subject so as to face the ureter. Furthermore, after identifying two or more ultrasonic elements facing the ureter in the Z-axis direction, the processing apparatus 2 analyzes reflection signals of ultrasonic waves transmitted from the two or more ultrasonic elements facing the ureter, to thereby determine an angle $\theta$ of the ureter with respect to an irradiation direction of each of the ultrasonic waves. Then, the processing apparatus 2 identifies Doppler shift frequencies generated in the ultrasonic waves reflected by the urine, to thereby determine the velocity of the urine flowing through the ureter and the flow quantity of the urine. Then, the processing apparatus 2 may display, on the display unit 22, information relevant to the flow quantity or velocity of the urine (such as waveform data indicating a change in the flow quantity of the urine over time).

The invention claimed is:

1. A physiological information processing method for automatically acquiring information relevant to a fluid flowing through a body of a subject using an ultrasonic sensor, wherein the ultrasonic sensor comprises a plurality of ultrasonic elements each configured to emit an ultrasonic wave toward a physiological tissue of the subject, the method being performed by a computer and comprising:

acquiring reflection signals of ultrasonic waves reflected by the physiological tissue;

identifying, among the ultrasonic elements, two or more ultrasonic elements facing a vessel through which the fluid flows, based on the reflection signals;

analyzing a reflection signal of an ultrasonic wave emitted from a first ultrasonic element of the two or more ultrasonic elements to thereby identify a first position of a portion of the vessel facing the first ultrasonic element in an irradiation direction of the ultrasonic wave;

analyzing a reflection signal of an ultrasonic wave emitted from a second ultrasonic element of the two or more ultrasonic elements to thereby identify a second position of a portion of the vessel facing the second ultrasonic element in the irradiation direction of the ultrasonic wave;

identifying an angle of the vessel with respect to the irradiation direction of the ultrasonic wave emitted from the first ultrasonic element or the second ultrasonic element, based on the first position and the second position;

analyzing the reflection signal of the ultrasonic wave emitted from the first ultrasonic element or the second ultrasonic element to thereby identify a Doppler shift frequency generated in the ultrasonic wave reflected by the fluid flowing through the vessel; and acquiring information relevant to the fluid at least based on the angle of the vessel and the Doppler shift frequency.

2. The physiological information processing method according to claim 1, wherein the information relevant to the fluid includes velocity of the fluid.

3. The physiological information processing method according to claim 2, wherein:

the information relevant to the fluid includes a flow quantity of the fluid;

the physiological information processing method further comprises identifying a sectional area of the vessel; and the flow quantity of the fluid is identified based on the sectional area of the vessel and the velocity of the fluid.

4. The physiological information processing method according to claim 3, wherein the identifying the sectional area of the vessel comprises:

analyzing the reflection signal of the ultrasonic wave emitted from the first ultrasonic element to thereby identify a position of an anterior side wall and a position of a posterior side wall in the portion of the vessel facing the first ultrasonic element;

identifying a distance between the position of the anterior side wall and the position of the posterior side wall; and identifying the sectional area of the vessel based on the angle of the vessel with respect to the irradiation direction and the distance between the position of the anterior side wall and the position of the posterior side wall.

5. The physiological information processing method according to claim 3, further comprising:

outputting information relevant to the flow quantity of the fluid.

6. The physiological information processing method according to claim 5, wherein the outputting the information relevant to the flow quantity of the fluid comprises visually presenting waveform data indicating a change in the flow quantity of the fluid over time.

7. The physiological information processing method according to claim 5, wherein the outputting the information relevant to the flow quantity of the fluid comprises audibly outputting an alert in response to determining that the flow quantity of the fluid is equal to or smaller than a threshold.

8. The physiological information processing method according to claim 1, wherein the identifying the first position in the irradiation direction comprises:

analyzing the reflection signal of the ultrasonic wave emitted from the first ultrasonic element to thereby identify a position of a first anterior side wall and a position of a first posterior side wall in the irradiation direction, in the portion of the vessel facing the first ultrasonic element; and identifying a position of a first midpoint between the first anterior side wall and the first posterior side wall in the irradiation direction, the identifying the second position in the irradiation direction comprises:

analyzing the reflection signal of the ultrasonic wave emitted from the second ultrasonic element to thereby identify a position of a second anterior side wall and a position of a second posterior side wall in the irradiation direction, in the portion of the vessel facing the second ultrasonic element; and identifying a position of a second midpoint between the second anterior side wall and the second posterior side wall in the irradiation direction, and the angle of the vessel with respect to the irradiation direction of the ultrasonic wave is identified based on the position of the first midpoint and the position of the second midpoint.

9. The physiological information processing method according to claim 1, wherein the Doppler shift frequency is identified through a pulsed Doppler method or a color Doppler method.

10. The physiological information processing method according to claim 1, wherein only the two or more ultrasonic elements facing the vessel are driven after the two or more ultrasonic elements facing the vessel are identified.

11. The physiological information processing method according to claim 1, wherein the fluid is blood or urine, and the vessel is a blood vessel or a ureter.

12. The physiological information processing method according to claim 11, wherein the ultrasonic sensor is attached to a neck portion of the subject, and the vessel is a carotid artery.

13. A non-transitory computer readable medium storing a computer implemented program for causing a computer to execute the physiological information processing method according to claim 1.

14. A physiological information processing apparatus that is configured to automatically acquire information relevant to a fluid flowing through a body of a subject using an ultrasonic sensor, wherein the ultrasonic sensor comprises a sheet, and a plurality of ultrasonic elements arranged in a two-dimensional pattern on the sheet and each configured to emit an ultrasonic wave toward a physiological tissue of the subject, the apparatus comprising:

at least one processor; and a memory that stores a computer-readable instruction that when executed by the processor, causes the apparatus to perform operations comprising:

acquiring reflection signals of ultrasonic waves reflected by the physiological tissue;

identifying, among the ultrasonic elements, two or more ultrasonic elements facing a vessel through which the fluid flows, based on the reflection signals;

analyzing a reflection signal of an ultrasonic wave emitted from a first ultrasonic element of the two or more ultrasonic elements to thereby identify a first position of a portion of the vessel facing the first ultrasonic element in an irradiation direction of the ultrasonic wave;

analyzing a reflection signal of an ultrasonic wave emitted from a second ultrasonic element of the two or more ultrasonic elements to thereby identify a second position of a portion of the vessel facing the second ultrasonic element in the irradiation direction of the ultrasonic wave;

identifying an angle of the vessel with respect to each of the irradiation direction of the ultrasonic wave associated with the first ultrasonic element or the second ultrasonic element, based on the first position and the second position;

analyzing the reflection signal of the ultrasonic wave emitted from the first ultrasonic element or the second ultrasonic element to thereby identify a Doppler shift frequency generated in the ultrasonic wave reflected by the fluid flowing through the vessel; and acquiring information relevant to the fluid at least based on the angle of the vessel and the Doppler shift frequency.

* * * * *